(12) United States Patent
Levy et al.

(10) Patent No.: US 9,651,197 B2
(45) Date of Patent: May 16, 2017

(54) DISPOSABLE CARTRIDGE FOR HOLDING COMPRESSED MEDICAL GAS

(76) Inventors: Frank Levy, Fort Myers, FL (US); Kimberley Levy, Fort Myers, FL (US)

(*) Notice: Subject to any disclaimer, the term of this patent is extended or adjusted under 35 U.S.C. 154(b) by 783 days.

(21) Appl. No.: 13/569,444

(22) Filed: Aug. 8, 2012

(65) Prior Publication Data

US 2013/0025600 A1    Jan. 31, 2013

Related U.S. Application Data

(63) Continuation-in-part of application No. 13/068,680, filed on May 17, 2011, now Pat. No. 8,876,749, which is a continuation-in-part of application No. 12/652,845, filed on Jan. 6, 2010, now abandoned, which is a continuation-in-part of application No. 12/210,368, filed on Sep. 15, 2008, now abandoned, which is a continuation-in-part of application No.
(Continued)

(51) Int. Cl.
| | |
|---|---|
| *F17C 1/00* | (2006.01) |
| *F17C 13/06* | (2006.01) |
| *A01N 25/00* | (2006.01) |
| *A61L 31/02* | (2006.01) |
| *F17C 5/06* | (2006.01) |
| *A61K 9/12* | (2006.01) |

(52) U.S. Cl.
CPC .............. *F17C 13/06* (2013.01); *A01N 25/00* (2013.01); *A61L 31/022* (2013.01); *F17C 5/06* (2013.01); *A61K 9/124* (2013.01); *F17C 2201/0104* (2013.01); *F17C 2201/058* (2013.01); *F17C 2203/0646* (2013.01); *F17C 2221/011* (2013.01); *F17C 2221/013* (2013.01); *F17C 2270/02* (2013.01)

(58) Field of Classification Search
CPC ...... B65D 17/165; B65D 17/18; B65D 39/02; B65D 5/748; B65D 5/749; B67B 7/24; B67B 7/28; B67B 2251/0015; F17C 2203/0617; F17C 2209/2181; F17C 2209/221; F17C 2223/0123
USPC ........ 220/284, 278, 277, 265, 581; 215/297, 215/296
See application file for complete search history.

(56) References Cited

U.S. PATENT DOCUMENTS 2,688,428 A * 9/1954 Manhartsberger ............ 141/352
3,004,686 A   10/1961 McKee
(Continued)

FOREIGN PATENT DOCUMENTS

| CN | 2179152 Y | 10/1994 |
|---|---|---|
| DE | 10161027 | 6/2003 |

(Continued)

*Primary Examiner* — Anthony Stashick
*Assistant Examiner* — Kaushikkumar Desai
(74) *Attorney, Agent, or Firm* — Welsh Flaxman & Gitler LLC

(57) ABSTRACT

A disposable cartridge for holding compressed medical gas includes a substantially cylindrical canister. The canister is delivered by an elongate cylindrical body that is tapered to a reduced diameter end portion having a discharge port or opening formed therein. The discharge port is covered by a pierceable tip that seals the canister to hold compressed medical gas with an interior chamber of the canister. The tip is selectively punctured to discharge the medical gas through the opening for use in a medical procedure.

4 Claims, 1 Drawing Sheet

Related U.S. Application Data

11/945,674, filed on Nov. 27, 2007, now Pat. No. 7,543,760.

(60) Provisional application No. 60/867,323, filed on Nov. 27, 2006.

(56) References Cited

U.S. PATENT DOCUMENTS

| | | | |
|---|---|---|---|
| 4,189,068 A * | 2/1980 | Apellaniz | 222/83.5 |
| 4,744,356 A * | 5/1988 | Greenwood | 128/204.26 |
| 5,246,140 A * | 9/1993 | Thix et al. | 222/4 |
| 5,580,530 A * | 12/1996 | Kowatsch et al. | 422/559 |
| 6,378,570 B1 * | 4/2002 | Shipachev et al. | 141/3 |
| 6,572,873 B1 * | 6/2003 | Osman et al. | 424/423 |
| 2005/0000981 A1 | 1/2005 | Peng et al. | |
| 2005/0119607 A1 * | 6/2005 | Van Der Linden et al. | 604/23 |
| 2006/0004322 A1 * | 1/2006 | Uesugi et al. | 604/26 |

FOREIGN PATENT DOCUMENTS

| | | | | |
|---|---|---|---|---|
| DE | 10161027 A1 * | 6/2003 | | B63C 9/18 |
| EP | 2468204 A1 | 6/2012 | | |

* cited by examiner

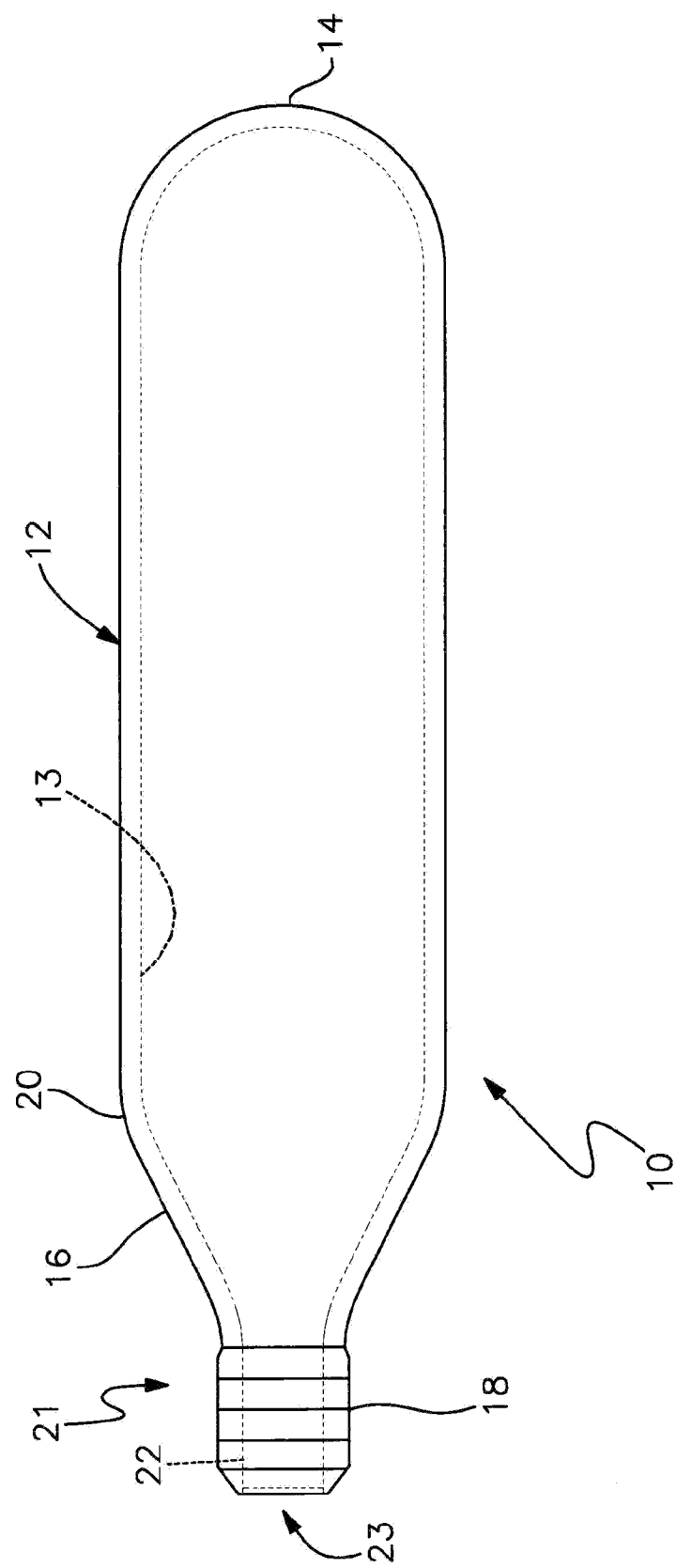

DISPOSABLE CARTRIDGE FOR HOLDING COMPRESSED MEDICAL GAS

RELATED U.S. APPLICATIONS

This application is a continuation-in-part of U.S. patent application Ser. No. 13/068,680 filed May 17, 2011, now U.S. Pat. No. 8,876,749 which is a continuation in part of U.S. patent application Ser. No. 12/652,846 filed Jan. 8, 2010, now abandoned which is a continuation in part of U.S. patent application Ser. No. 12/210,368 filed Sep. 15, 2008, now abandoned, which is a continuation in part of U.S. patent application Ser. No. 11/945,674 filed Nov. 27, 2007, now U.S. Pat. No. 7,543,760, which claims the benefit of U.S. Provisional Patent Application Ser. No. 60/807,323 filed Nov. 27, 2006, the disclosures of which are incorporated herein by reference in their entirety.

FIELD OF THE INVENTION

This invention relates to a disposable aluminum cartridge for accommodating compressed medical gases such as carbon dioxide, oxygen, nitrous oxide and the like.

BACKGROUND OF THE INVENTION

Large pressurized tanks conventionally contain compressed gases for use in medical treatments and procedures. These tanks are usually heavy, bulky end quite inconvenient to transport. They can also present a dangerous risk of explosion. Refilling such tanks also tends to be time consuming and logistically inconvenient. In addition, pressurized full-sized tanks are also apt to harbor mold, debris and rust within the tank. This can seriously jeopardize the quality and integrity of the accommodated gas. Contaminants are highly undesirable in medical applications where toe gas should exhibit a high degree of purity.

SUMMARY OF THE INVENTION

It is therefore an object of the present invention to provide a compact disposable cartridge for conveniently containing various types of medical gas in a compressed condition such that the gas is readily and conveniently available for use assorted medical applications.

It is a further object of this invention to provide a cartridge for compressed medical gas that is compact, lightweight and easy to transport, use and replace so medical procedures.

It is a further object of this invention to provide a cartridge for compressed medical gas that is extremely safe to use and which greatly reduces the risk of explosion.

It is a further object of this invention to provide a disposable cartridge for compressed medical gas that does not require tedious and time consuming refilling.

It is a further object of this invention to provide a cartridge for compressed medical gas, which eliminates or at least greatly reduces the formation of mold and the collection of rust and debris therein such that the gas is maintained in a sterile and extremely pure condition for medical use.

This invention features a disposable cartridge for accommodating a compressed medical gas. The medical gas may include carbon dioxide, oxygen, nitrous oxide or any other gas that must be stored in a pressurized condition for medical use. The cartridge includes an elongate, generally cylindrical body that is tapered toward and joined to a reduced diameter and substantially cylindrical end portion. The end portion includes an opening communicably connected to an inferior chamber of the cartridge body. The openings sealed by a pierceable tip. The tip is selectively punctured to open the cartridge such that compressed medical gas contained within the interior chamber of the cartridge body may be delivered through the tip for use in a medical procedure or application.

In a preferred embodiment, the cartridge body and reduced end portion include a triple-washed aluminum canister for holding a medical grade gas under pressure. The canister may weigh between 12 to 50 grams and is preferably about 25 grams.

The reduced diameter portion of the canister may be encircled by a thread for attaching the cartridge to a medical apparatus requiring compressed medical gas of the type contained by the cartridge. The optimum thread size is approximately ⅜", although it can vary from about ¼" to 1".

DETAILED DESCRIPTION OF PREFERRED EMBODIMENTS

Other objects, features and advantages will occur from the following description of a preferred embodiment and the accompanying drawings, in which:

FIG. 1 is a side elevational view of a preferred disposable cartridge for accommodating compressed medical gas in accordance with this invention.

There is shown in FIG. 1 a disposable aluminum cartridge 10 for accommodating a compressed medical gas. It should be understood that cartridge 10 is suitable for holding a wide variety of medical gases including, but not limited to, carbon dioxide, oxygen and nitrous oxide. Cartridge 10 is capable of holding virtually any type of medical gas in a pressurized condition for use in various types of medical procedures. The type of gas and the type of medical applications involved are not limitations of this invention.

Cartridge 10 includes a generally cylindrical canister body 12 having an elongate shape with a rounded bottom 14. The canister body encloses an interior chamber 13 for holding a compressed medical gas. The body includes a tapered neck portion 16 that is joined to and terminates in a reduced diameter cylindrical end portion 18. Body 12, tapered portion 10 and reduced diameter portion 18 thereby define a canister 20 that is preferably composed of aluminum. The end portion is preferably encircled by a thread 21 that allows canister 20 to be screwed into a complementary threaded opening of a piece of medical equipment with which the canister is engaged. The optimum thread size is ⅜" although it can vary from ¼" to 1" within the scope of this invention.

In radiological applications, canister 20 may be used to hold carbon dioxide in chamber 13 and the threaded reduced diameter end portion 18 may be engaged with the portable medical gas delivery system produced under the trademark $CO_2$mmander® as disclosed in pending application Ser. Nos. 13/068,880 and 12/652,845, the disclosures of which are incorporated herein by reference. Although the cartridge is particularly convenient and effective for use with this system, it may be used in a wide variety of other medical applications and for holding venous other types of compressed medical gases.

Reduced diameter portion 21 includes an opening 22 in communication with interior chamber 13. The distal end of reduced diameter portion 21 of canister 20 carries a pierceable tip 23 that seals opening 22 after pressurized medical gas has been introduced into the interior of canister 12. Tip 23 may comprise a fairly thin and flexible foil that is securely sealed over opening 22 in end portion 18. Tip 23 is readily punctured in a conventional manner to open canister 12 so that compressed gas within the canister is made available for delivering through opening 22 to a desired medical application or use.

Canister 12 is composed and constructed to provide significant advantages. In particular, the canister has a relatively compact size and configuration and is extremely lightweight especially when compared with standard full-sized tanks conventionally used to contain compressed medical gases. In particular, the preferred weight of canister 12 is 25 grams, although it can range from 12 to 50 grams. The canister employs a triple-washed aluminum construction, which maintains the sterility and purity of gases contained within the canister. In particular, the triple-washed canister resists the formation of mold and rust, as well as the collection of other types of debris within the interior chamber 13 of the canister. As a result, the integrity of the canister is maintained so that the contained gas is suitable for medical use wherein nigh levels of purity and sterility are indispensable.

The compact and relatively small size of the cartridge allows the cartridge to be transported and manipulated easily and conveniently. Replacement and disposal of the cartridge are facilitated. Bulky, heavy and cumbersome tanks are avoided.

The compact cartridge is disposable and therefore does not have to be refilled or cleaned between uses. This reduces the time, logistic complexity and tedium required to transport and refill conventional tanks. It also helps to maintain the sterility and purity of the compressed medical gas contained within the cartridge. The lightweight, disposable aluminum cartridge disclosed herein therefore provides for a number of significant advantages over the large bulky and cumbersome tanks used in the prior art.

From the foregoing it may be seen that the apparatus of this invention provides for a disposable aluminum cartridge for accommodating compressed medical gases such as carbon dioxide, oxygen, nitrous oxide and the like. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

What is claimed is:

1. A disposable cartridge accommodating a medical gas, said cartridge comprising:
an elongate, generally cylindrical body having an interior chamber accommodating a compressed and sterile medical grade gas therein, said body being inwardly tapered proximate one end thereof and joined to a reduced diameter and generally cylindrical leading end portion, said leading end portion including an opening communicably connected to said interior chamber of said cartridge body, said opening being sealed by a pierceable tip, said tip being selectively punctured to open said cartridge such that the compressed medical gas contained within said interior chamber of said cartridge is deliverable through said tip for use in a medical procedure, wherein said cylindrical body and said end portion include a triple washed aluminum construction for holding the medical grade gas within said interior chamber of said cylindrical body under pressure;
said cartridge having a weight with said medical grade gas sealed therein of at least twelve grams and not greater than fifty grams.

2. The cartridge of claim 1 in which said end portion of said canister is encircled by a thread for attaching said cartridge to a medical apparatus requiring compressed gas of the type contained by said cartridge.

3. The cartridge of claim 2 in which said thread is at least ¼" (6.35 mm) and not greater than 1" (25.4 mm).

4. A supply of pressurized medical gas comprising:
a cartridge including an elongate, generally cylindrical body with an interior chamber formed therein, said body having an inwardly tapered section that interconnects said body to a generally cylindrical reduced diameter end portion, said end portion including an opening formed therethrough, which opening communicates with said interior chamber of said body, wherein said cylindrical body and said end portion include a triple washed aluminum construction for holding medical grade gas within said interior chamber of said cylindrical body under pressure; and
a compressed and sterile medical grade gas contained within said interior chamber, said cartridge including a pierceable tip for sealing said medical grade gas under pressure within said chamber, said tip being selectively punctured to open said cartridge such that said compressed and sterile medical grade gas contained within said medical chamber of said cartridge body is deliverable through said tip for use in a medical procedure;
said cartridge having a weight with said medical grade gas sealed therein of at least twelve grams and not greater than fifty grams.

* * * * *